United States Patent [19]

Singh et al.

[11] 4,374,987

[45] Feb. 22, 1983

[54] PROCESS FOR THE PREPARATION OF HIGH PURITY METHOTREXATE AND DERIVATIVES THEREOF

[75] Inventors: Balwant Singh, Stamford; Frederic C. Schaefer, Darien, both of Conn.

[73] Assignee: American Cyanamid Company, Stamford, Conn.

[21] Appl. No.: 178,070

[22] Filed: Aug. 14, 1980

[51] Int. Cl.³ .......................................... C07D 475/08
[52] U.S. Cl. .................................................. 544/260
[58] Field of Search ........................................ 544/260

[56] References Cited

U.S. PATENT DOCUMENTS 2,570,391  10/1951  Seeger .................................. 544/260

*Primary Examiner*—Paul M. Coughlan, Jr.
*Attorney, Agent, or Firm*—Jack W. Richards

[57] ABSTRACT

An improved process for the preparation and purification of N-{p-([2,4-diamino-6-pteridinyl)-methyl]methylamino)benzoyl} glutamic acid, also known as methotrexate, using the alkali metal, calcium and zinc salts of N-methyl-p-aminobenzoylglutamate, tetraaminopyrimidine sulfate, 1,1,3-tribromoacetone and the alkali metal and zinc salts of methotrexate.

2 Claims, No Drawings

PROCESS FOR THE PREPARATION OF HIGH PURITY METHOTREXATE AND DERIVATIVES THEREOF

BACKGROUND OF THE INVENTION

Methotrexate is a well-known anti-cancer drug useful in the treatment of various forms of cancer. The process of the present invention is expected to considerably simplify the existing processes resulting in higher productivity and reduced costs.

The present invention is an improved process over the present commercial processes for the preparation of methotrexate such as the dibromopropionaldehyde process. It is considerably simpler, requires no extraordinary control to avoid loss of yield and produces methotrexate of high purity in a moderately high yield. A number of reactants needed in the dibromopropionaldehyde process have been eliminated.

The dibromopropionaldehyde process produces dihydromethotrexate which must be oxidized in situ with an oxidizing agent such as potassium triiodide. This oxidation step is extremely sensitive and must be appropriately controlled otherwise yields of methotrexate are substantially reduced. In contrast, the process of the present invention produces methotrexate directly and the process is easy to control. Purification is achieved via the insoluble zinc salt and crystallization of the sodium salt. The process results in high purity 98+% methotrexate.

The following patents and publications are presented herein to further develop the background of the present invention and establish the state of the existing art.

J.A.C.S. 71 1753-1758 (1949) discloses the preparation of methotrexate using 2,4,5,6-tetraaminopyrimidine sulfate, 2,3-dibromopropionaldehyde, p-(N-methylamino)-benzoylglutamic acid and barium chloride; and the preparation of aminopterin using 2,4,5,6-tetraaminopyrimidine sulfate, 1,1,3-tribromoacetone, p-aminobenzoyl-L(+)-glutamic acid and barium chloride.

C.A. 70 106833j (1970) discloses the preparation of methotrexate using tetraaminopyrimidine, trichloroacetone, and the barium salt of (N-methylamino)-benzoylglutamic acid.

U.S. Pat. No. 2,443,165 discloses a process for preparing pterins by reacting 2,4,5-triamino-6-hydroxypyrmidine with a trihaloacetone and aminobenzoic acid or one of its amides.

U.S. Pat. No. 2,512,572 describes the preparation of substituted pterins by simultaneously reacting a disubstituted 4,5-diaminopyrimidine, a dihaloproprionaldehyde, and a secondary amine.

U.S. Pat. No. 2,956,957; U.S. Pat. No. 2,719,157; and U.S. Pat. No. 2,443,165 disclose the reaction of various halo-substituted aldehydes and ketones, including 1,1,3-trichloro and 1,1,3-tribromoacetone with 2,4,5-triamino-6-hydroxypyrimidine, and p-aminobenzoyl glutamic acid to obtain folic acid.

U.S. Pat. No. 3,892,801 discloses the preparation of the zinc salt of p-aminobenzoylglutamic acid in preparation of the alkali metal salt of p-methylaminobenzoylglutamic acid used as an intermediate in the synthesis of methotrexate.

U.S. Pat. No. 4,136,101 discloses the preparation of diethyl N-(p-methylaminobenzoyl)glutamate, useful as an intermediate in the preparation of methotrexate, using zinc N-(p-methylaminobenzoyl)glutamate.

SUMMARY OF THE INVENTION

This disclosure emphasizes the preparation of methotrexate and its purification. However, certain derivatives of methotrexate may also be prepared and purified according to the process of this invention.

This invention contemplates the preparation of methotrexate and derivatives thereof having the formula:

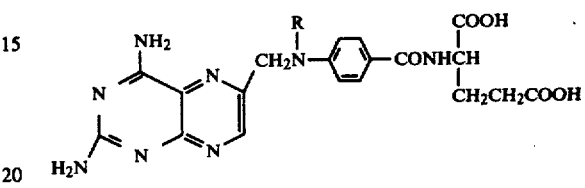

wherein R is hydrogen or $C_1$-$C_4$ alkyl which comprises simultaneously reacting 2,4,5,6-tetraaminopyrimidine sulfate and 1,1,3-tribromoacetone with a salt selected from the group consisting of

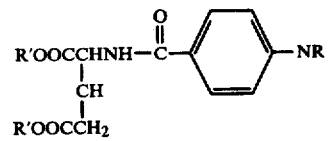

wherein R is hydrogen or $C_1$-$C_4$ alkyl and R' is an alkali metal, calcium or zinc; and the purification of the resultant methotrexate or derivative thereof. In the above formula, preferably R is methyl and R' are both zinc or sodium.

The above reaction can be illustrated with reference to Flow Sheet I wherein in the initial reaction methotrexate (MTX) (IV) is prepared in a one-pot simultaneous reaction of 2,4,5,6-tetraaminopyrimidine sulfate (TAP.H$_2$SO$_4$) (I) with 1,1,3-tribromoacetone (TBA) (II) and zinc N-methyl-p-aminobenzoylglutamate (ZnNMe PABG) (III).

FLOW SHEET I

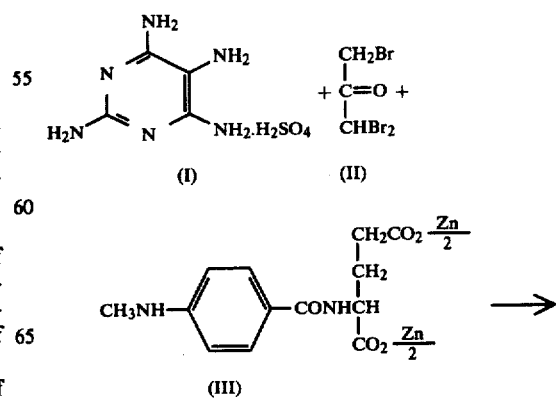

-continued
FLOW SHEET I

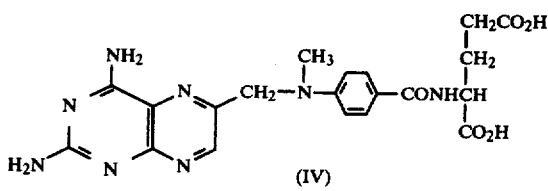

(IV)

With reference to Flow Sheet I, the TAP.H$_2$SO$_4$ added is only slightly soluble and gradually dissolves as the reaction proceeds. The TAP.H$_2$SO$_4$ (I), TBA (II) and ZnNMePABG (III) are reacted at a temperature range of from about 30° C. to about 60° C., preferably about 30° C. to about 50° C. and in a pH range of from about 1.5 to about 4.0, preferably about 1.5 to about 3.5. The reaction pH of the reaction mixture is maintained by the addition of sodium hydroxide. The time can vary from about 1 to about 5 hours. The reaction is carried out by simultaneously mixing the three reactants together, preferably in the presence of water. The water serves as a solvent for the reactants and/or the reaction product and allows for more selective reaction and reduction of by-product impurities. Alternatively, the TBA. may be added portion wisee tto the reaction mixture. Diluents for TBA. may include methyl or ethyl alcohol or acetic acid.

With reference to Flow Sheet I, after the initial reaction, the purification of methotrexate proceeds as follows. Concentrated ammonium hydroxide is added to about pH 9.5 to solubilize product methotrexate, and the mixture is filtered. The filtrate is adjusted to about pH 6 with cencentrated hydrochloric acid, and precipitated zinc methotrexate is filtered and washed. The zinc salt is reslurried in water and dissolved by addition of concentrated hydrochloric acid to about pH 1.5. Crude methotrexate hydrochloride which crystallizes is reslurried in water, and dissolved by adding caustic to about pH 10. Concentrated hydrochloric acid is then added to about pH 1.5 to recrystallize more pure methotrexate hydrochloride. The hydrochloride is slurried in water and dissolved by adding soidum hydroxide to about pH 10. Acetone is added to about 1-1.5 ml./ml. of aqueous solution, the mixture is stirred and then clarified. Acetone is added to the filtrate to about 75-88 vol. % to crystallize disodium methotrexate, which is filtered. The disodium methotrexate is dissolved in water and 3% sulfuric acid added to about pH 4. High purity methotrexate is isolated by filtration.

The purification procedure used may also be used in a similar manner to purify methotrexate prepared by processes other than that of the present invention. The purification procedure of the instant invention can be used after the initial preparation of the crude methotrexate reaction product mixture prepared as disclosed in, for example, J.A.C.S. 71, 1753–1758 (1949).

In the preparation of methotrexate by the method of JACS, 71 1753 (1949), or by various other processes, or by the process of this invention, the desired methotrexate is accompanied by a variety of by-products. It has now been found that precipitation of the very insoluble zinc salt of methotrexate (ZnMTX) at about pH 6 permits removal of much of this contamination by washing and is a very advantageous purification step in the recovery of medicinal grade methotrexate.

The zinc required for precipitation of ZnMTX may be added to the solution in various forms e.g., the soluble zinc salts, zinc chloride, zinc acetate, zinc sulfate, and the like. However, it is particularly advantageous to incorporate it in the form of ZnN-MePABG since this zinc salt is conveniently used in the preparation and purification of the intermediate glutamic acid derivative and thus is the most available form of this reactant. If the zinc salt is not added in the form of ZnN-MePABG, it is preferably added in the purification stage just after the addition of the ammonium hydroxide. The amount of the soluble zinc salt added should be at least equivalent to the amount of expected MTX. By using the zinc salt, preparation of the reagent is simplified and zinc is introduced for latter advantageous use in product isolation. Use of zinc to allow isolation of ZnMTX enables removal of major amounts of impurities which are co-precipitated with MTX in conventional recovery procedures.

In the purification of MTX to medical specifications it has been found that isolation and recrystallization of the sodium salt, Na$_2$MTX, provides a highly advantageous step in the purification process. A concentrated aqueous solution of the crude sodium salt can be refined by precipitation of tarry by-products by addition of a small proportion of ethanol or acetone after which further addition of the organic diluent causes crystallization of Na$_2$MTX, leaving other by-products in the mother liquor.

The sodium salt can be recrystallized in the same manner to progressively higher purity if desired or can be converted readily to other forms of the drug such as free MTX or MTX.HCl. The sodium salt is desirable as such because of its ready solubility in water for administration.

The use of Na$_2$MTX crystallization and recrystallization from acetone/H$_2$O or ethanol/H$_2$O mixtures provides a novel method to obtain high purity product.

The intermediate isolation of zinc methotrexate, methotrexate hydrochloride and/or sodium methotrexate enables one to obtain a high purity product. After purification methotrexate can be isolated in the form desired such as the free base, hydrochloride, or sodium salt.

The process of the present invention possesses other advantages over the prior art process for the preparation of methotrexate in addition to those mentioned heretofore.

In the preparation of 2,4-diamino-pteridines it has been conventional to use a water-soluble salt of tetraaminopyrimidine such as the hydrochloride or the sulfite. Frequently the hydrochloride has been prepared in a preliminary step by a metathesis reaction of TAP.H$_2$SO$_4$ with a soluble barium salt whereby barium sulfate is precipitated and TAP solubilized. It has now been discovered that use of the relatively insoluble sulfate salt itself is advantageous, in that thereby the concentration of dissolved tetraaminopyrimidinium ions is maintained at a favorable level; as this reagent is consumed in the reaction, more sulfate salt dissolves to maintain a saturated solution. In this way side reactions that are caused by high TAP concentration are minimized.

The actual solubility of TAP.H$_2$SO$_4$ is a function of the temperature and pH of the reaction solution, through which its value can be controlled for best results. For the methotrexate (MTX) process described herein best conditions were in the vicinity of 50° C. and pH 2.0.

DETAILED DESCRIPTION OF THE INVENTION

The improved process of this invention may be illustrated in more detail by reference to the following specific example.

EXAMPLE

Preparation of Methotrexate (MTX)

Initial Reaction

Charge 24.2 g. (0.096 mole) TAP.H$_2$SO$_4$ and 15.9 g. (0.0366 mole) ZnN-MePABG with 270 cc of water to a 1 liter flask equipped with stirrer, thermometer and combination pH electrode. Warm the suspension to 50° C. and adjust the pH to 2.0 with 12 N hydrochloric acid (~9 cc.).

Dissolve 26.6 g. (0.088 mole) TBA in 27 cc of ethanol and add one-half of the solution to the reaction mixture. Hold the pH at 2.00×0.05 by addition of 20% sodium hydroxide as needed while maintaining the reaction temperature at 50°×1°. After 15 minutes, add the remainder of the TBA-ethanol solution. Continue reaction until approximately 45 cc of 20% NaOH have been consumed and the required rate of addition has slowed to less than 1 cc/15 minutes (about 3-3.5 hours usually required).

Purification Stage

Cool to 30°-40° C. and add 60 cc. of 29% NH$_4$OH gradually with continuous stirring to pH 9.5, cooling if necessary to keep the temperature below 50°. Stir at room temperature for 15 minutes, or longer if necessary to obtain a uniform suspension. Add 10 g. Hyflo, stir 15 minutes longer to complete extraction of MTX and insolubilization of by-products. Filter and wash insolubles with water (~50 cc.). Discard the filter cake (~26 g. wet; dry weight about 6 g.).

Stir the filtrate (~600 g.) at room temperature and acidify gradually with 12 N hydrochloric acid to pH 6.0 (~41 cc. required), producing a thick suspension of crude zinc methotrexate (ZnMTX). Filter and wash thoroughly with water.

Reslurry the damp ZnMTX filter cake (~110 g.) in 400 cc. of water and gradually acidify to pH 1.5 with 12 N hydrochloric acid (~8 cc., added over 10-15 minutes). The suspension thins markedly at pH 2.5-3, and as stirring is continued for 1-1.5 hours methotrexate hydrochloride ("MTX.HCl") gradually crystallizes. Filter and wash the cake with 80 cc. of water in several small portions (damp weight, 25 g.).

Disperse the damp MTX.HCl filter cake in 250 cc. of water, add 20% NaOH (~7 cc.) gradually to dissolve the solid and give pH 10, and dilute further to 400 g. of solution. Acidify to pH 1.5 slowly (~10 min.), stir 1.5 hours to complete recrystallization of MTX.HCl, and filter. Wash solid with 40 cc. of water in small portions.

Redissolve the MTX.HCl cake in water plus 20% NaOH to give 100 g. of solution at pH 10. Dilute with 125 cc. of acetone with stirring. Allow precipitated tar to settle for 30 minutes and filter. Dilute the filtrate further with an additional 175 cc. of acetone, added gradually with vigorous stirring. (The product is initially precipitated as an emulsion as a part of the acetone is added. Crystallization begins within a few minutes and the remainder of the acetone is not added until this has occurred). Stir the product suspension for one hour to complete crystallization. Filter, wash with 3/1 acetone-water and finally with acetone, and pump dry. Yield of Na$_2$MTX (hydrate), ~11.4 g.

Dissolve product Na$_2$MTX in 400 cc. of deionized water and acidify to pH 4.0 with 10% sulfuric acid (add slowly at pH 5.5-4.0). Stir for 15 minutes and filter. Wash well with water and with acetone and air-dry to give 9.1 g. of MTX hydrate (8.2 g. of real MTX of greater than 98% purity, 46% based on starting N-MePABG).

We claim:

1. A process for preparing a compound of the formula

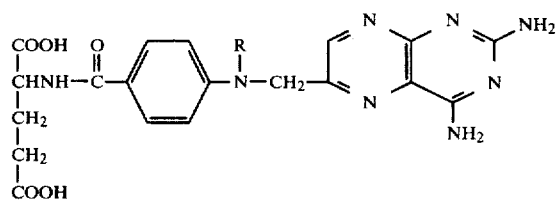

wherein R is hydrogen or C$_1$ to C$_4$ alkyl which comprises simultaneously reacting 2,4,5,6-tetraaminopyrimidine sulfate and 1,1,3-tribromoacetone with a salt of the formula

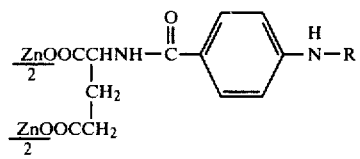

in water at a temperature of about 30° to about 60° C. and a pH of about 1.5 to about 3.5; adjusting the pH of the reaction mixture with ammonium hydroxide to a pH of from about 9 to about 10; lowering the pH of the filtrate to about pH 6.0 with hydrochloric acid to precipitate the zinc salt; filtering and water-washing the resultant precipitate; reslurrying said precipitate in water and adjusting the pH of the slurry to about pH 1.5 with hydrochloric acid, filtering and water-washing the resultant precipitate; dispersing the filtered and water-washed precipitate in water and adjusting the pH of the solution of pH of about 10 with sodium hydroxide; acidifying the solution to a pH of about 1.5 with hydrochloric acid; water-washing the resultant precipitate; redissolving said precipitate in water and adjusting the pH of the solution to about pH 10 with sodium hydroxide; diluting the solution with acetone and dissolving the precipitate in water; and acidifying to a pH of about pH 4.0 with sulfuric acid.

2. A process for preparing a compound of the formula:

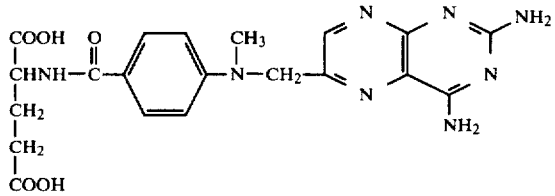

which comprises simultaneously reacting 2,4,5,6-tetraaminopyrimidine sulfate and 1,1,3-tribromoacetone with a salt of the formula

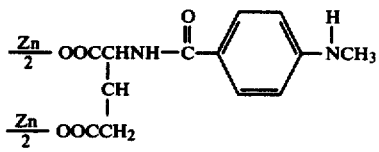

at a temperature of about 50° C. and a pH of about 2.0; adjusting the pH of the reaction mixture with ammonium hydroxide to a pH of from about 9 to about 10; lowering the pH of the filtrate to about pH 6.0 with hydrochloric acid to precipitate the zinc salt of methotrexate; filtering and water-washing the resultant precipitate; reslurrying said precipitate in water and adjusting the pH of the slurry to about pH 1.5 with hydrochloric acid; filtering and water-washing the resultant precipitate; dispersing the filtered and water-washed precipitate in water and adjusting the pH of the solution to pH of about 10 with sodium hydroxide; acidifying the solution to a pH of about pH 1.5 with hydrochloric acid; water-washing the resultant precipitate; redissolving said precipitate in water and adjusting the pH of the solution to about pH 10 with sodium hydroxide; diluting the solution with acetone and dissolving the precipitate in water; and acidifying to a pH of about pH 4.0 with sulfuric acid.

* * * * *